(12) United States Patent
Tominaga et al.

(10) Patent No.: US 6,875,328 B2
(45) Date of Patent: Apr. 5, 2005

(54) PH SENSOR (75) Inventors: Koji Tominaga, Kyoto (JP); Tsuyoshi Nakanishi, Kyoto (JP); Hiroki Tanabe, Kyoto (JP); Mitsuru Honjo, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/946,499

(22) Filed: Sep. 6, 2001

(65) Prior Publication Data

US 2002/0027074 A1 Mar. 7, 2002

(30) Foreign Application Priority Data

Sep. 6, 2000 (JP) .................................... P. 2000-270694
Jul. 30, 2001 (JP) .................................... P. 2001-228853

(51) Int. Cl.$^7$ ..................... G01N 27/404; G01N 27/414
(52) U.S. Cl. ..................... 204/433; 204/414; 204/416; 257/253
(58) Field of Search ................................ 204/416, 418, 204/419, 420, 433, 414; 257/253

(56) References Cited

U.S. PATENT DOCUMENTS

| | | | |
|---|---|---|---|
| 2,183,531 A | * | 12/1939 | Allison |
| 4,154,659 A | * | 5/1979 | Zetter |
| 4,288,308 A | * | 9/1981 | Hach |
| 4,474,183 A | * | 10/1984 | Yano et al. |
| 5,218,304 A | * | 6/1993 | Kinlen et al. |
| 5,248,403 A | * | 9/1993 | Tomita et al. |
| 5,507,936 A | * | 4/1996 | Hatschek et al. |

* cited by examiner

Primary Examiner—Kaj K. Olsen
(74) Attorney, Agent, or Firm—Sughrue Mion, PLLC

(57) ABSTRACT

An inexpensive, high-performance pH sensor measure the surface of a solid substance in a simple manner, comprising an ion sensing part 2 which responds to pH, a reference electrode 3, a gel-form ion permeable substance 10, which has a predetermined pH value and covers the ion sensing part 2 and reference electrode 3, and a cover member 9, which houses the ion permeable substance 10 and has an opening 9a formed at a position near the abovementioned ion sensing part 2.

22 Claims, 6 Drawing Sheets

PH SENSOR

BACKGROUND OF THE INVENTION

1. Field of the Invention

This invention concerns a pH sensor and more specifically to a pH sensor that is inexpensive and high in performance.

2. Description of the Prior Art

The pH values of solid substances have been measured in order to examine its properties. For example, FIG. 7 is a diagram for explaining the method of measuring the pH value a rice grain for determination of the freshness of the rice grain.

Figure 7:
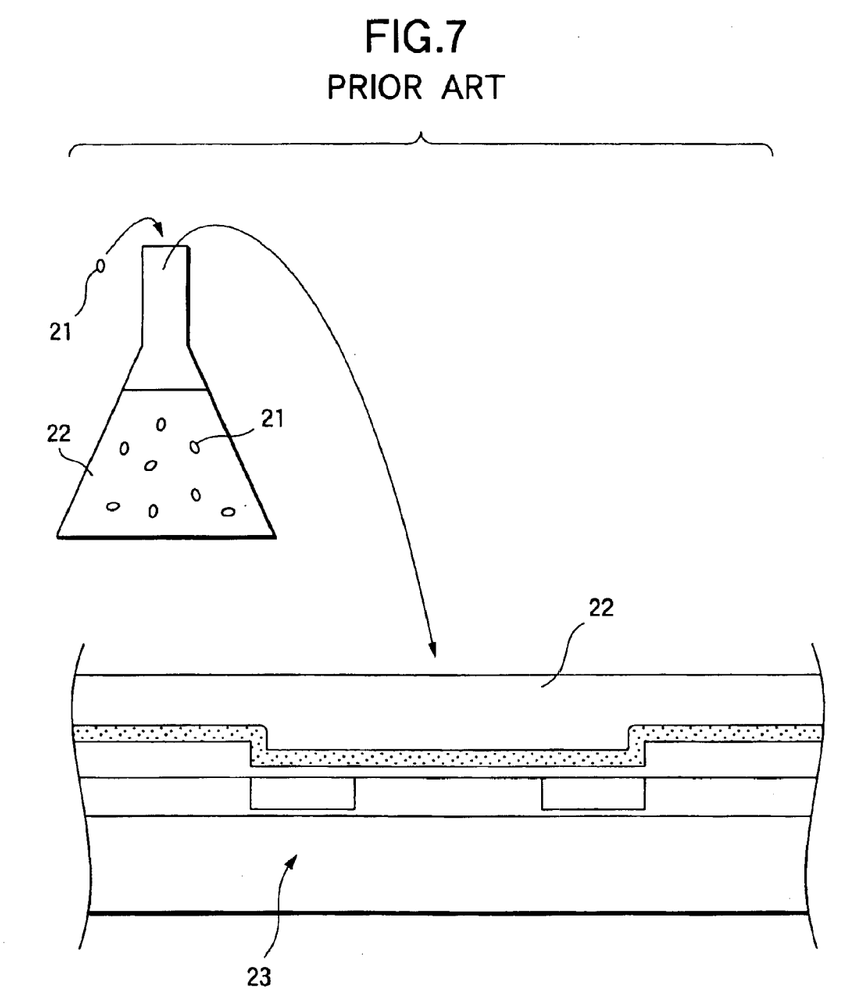
FIG. 7 is a diagram for explaining the measurement method using a prior-art pH sensor.

In FIG. 7, reference numeral 21 is a rice grain, which is the object to be measured, 22 is water or other solvent in which a plurality of rice grains 21 are placed, and 23 is an ISFET (Ion sensitive field effect transistor) for pH measurement. That is, since ISFET 23 and other pH sensors are conventionally arranged for measurement of the pH of a liquid, when a solid is measured as the measured object, it was measured via water or other solvent 22 or a cloth or paper immersed in solvent 22.

Also, with a pH meter that uses an ordinary pH sensor 23, a standard solution, with a known pH and a pH buffer action, was used to perform calibration of the sensor so that the exact measuring value can be obtained.

However, the conventional procedure of placing and stirring a solid substance once in a solvent 22 and measuring the pH upon taking out solvent 22 not only required a large amount of the sample to be measured but much trouble was required as well. The measurement of the pH of a solid substance in a direct and simple manner was thus desired. However, the above-described prior-art pH sensor 23 cannot satisfy this demand.

Also as a device for making rapid measurements of solid substances, there is the pH distribution analysis device, with which a thin membrane of agar is formed on a detection plane and laser light is illuminated in a scanning manner with the measured object being placed on the thin membrane to measure the two-dimensional pH distribution. However, this device was unavoidably large and complex in structure. That is, this analysis device was expensive and did not enable measurements in a simple manner.

Furthermore, with a pH meter using a prior-art pH sensor, calibration work using a standard solution was required in all cases, and this has been a cause that prevented pH measurements from being made in a simple manner.

SUMMARY OF THE INVENTION

This invention has been made in view of the above circumstances and an object thereof is to provide an inexpensive, high-performance pH sensor with which the measurement a solid substance can be performed in a more simple manner.

This invention provides means of the following arrangements in order to achieve the above object. That is, the first aspect of this invention provides a pH sensor comprised of an ion sensing part of an ion sensor, which responds to pH, a reference electrode, a gel-form ion permeable substance, which has a predetermined pH value and covers the ion sensing part and the reference electrode, and a cover member, which houses the ion permeable substance and has an opening formed at a position close to the abovementioned ion sensing part.

The second aspect of this invention provides a pH sensor comprised of an ISFET, arranged by the provision of an ion selective membrane, which responds to pH, on the gate of a field effect transistor, a gel-form ion permeable substance, which has a predetermined pH value and covers at least the abovementioned ion selective membrane and a reference electrode, and a cover member, which houses the ion permeable substance and has an opening formed at a position close to the abovementioned ion selective membrane.

Thus when an above-described pH sensor is used and an object to be measured is pressed against the opening formed on the cover member, the pH value of the ion permeable substance changes due to being affected by the pH of the surface of the measured object, and this change of pH value can then be measured by means of an ion sensing part such as the ISFET. Also, since the pH value of the ion permeable substance prior to making the measurement is known, this can be used as the reference pH value, thus doing away with the calibration of the pH sensor using the standard solution.

Furthermore, since the abovementioned ion permeable substance takes the form of a gel, measurements can be made in the condition where the ion sensing part such as the ISFET and the reference electrode, which are housed in the cover body, are covered with the ion permeable substance, and the change of the pH value of the ion permeable substance affects the relationship between the voltage applied to the reference electrode and the output of the ion sensing part. That is, the surface of a solid substance can be measured simply and at high sensitivity by measuring the change of the pH value of the abovementioned ion permeable substance.

In the case where the pH sensor is arranged as a pH sensor package with which at least the abovementioned reference electrode, ion permeable substance, and cover member are made exchangeable respectively for making measurements according to the object to be measured, the pH sensor package can be exchanged readily. A measured object can thus always be pressed against a new ion permeable substance that has not been changed in pH value and the measurement precision can thereby be optimized at all times.

DESCRIPTION OF THE PREFERRED EMBODIMENT

Figure 1:
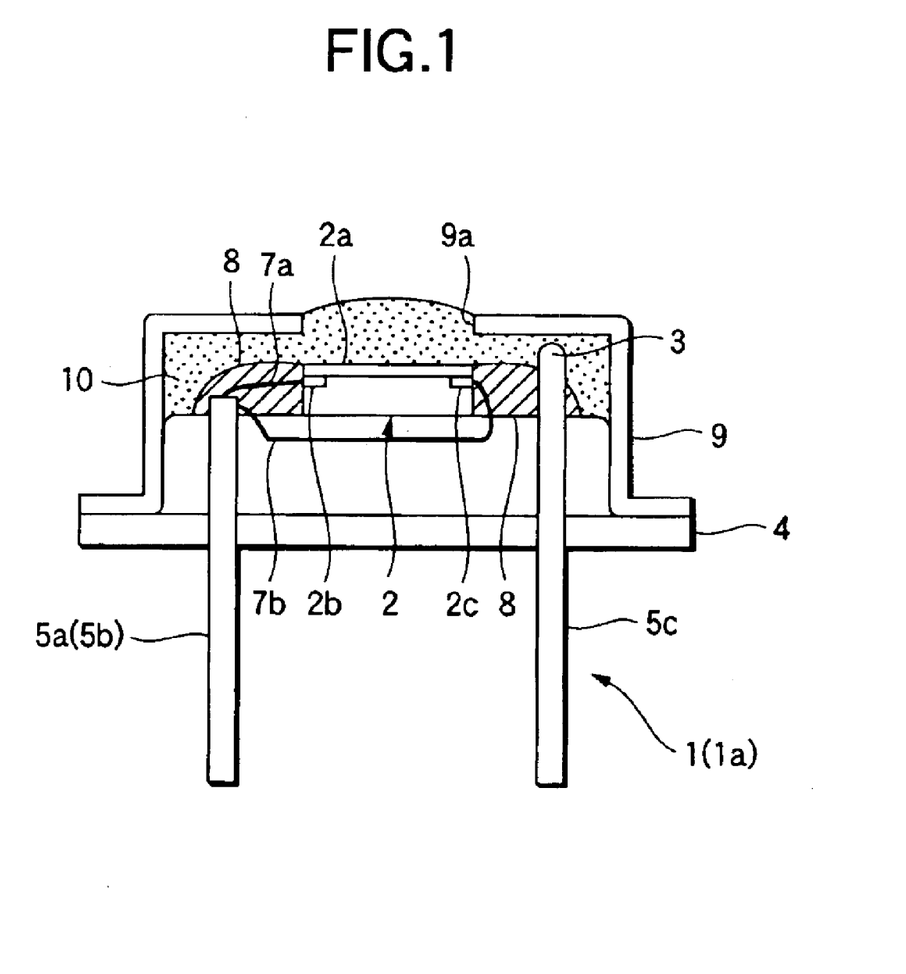
FIG. 1 is a vertical section, which shows an example of an arrangement of a pH sensor by this invention.

FIG. 1 is a diagram, which shows an example of a pH sensor 1 by this invention. In FIG. 1, reference numeral 2 is an ISFET, which is comprised of a silicon substrate and is an example of an ion sensing part, 3 is a reference electrode, 4 is a stem for fixing the ISFET 2, 5a to 5c are pins which are passed through stem 4 and are connected to ISFET 2 or reference electrode 3, 7a and 7b indicate leader lines that connect pins 5a and 5b to ISFET 2, and 8 is a sealing material, which provide insulation of the surroundings of leader lines 7 and secure watertightness at the connection part of the abovementioned pins 5a to 5c and stem 4. The pin 5a is connected to a source 2b of the ISFET 2 through the leader line 7a and the pin 5b is connected to a drain 2c of the ISFET 2 through the leader line 7b. A drain current flows between the pins 5a and 5b. The reference electrode 3 may have a general configuration. However, for example, the reference electrode may have a configuration in that the upper end of the abovementioned pin 5c is protruded from sealing material 8 and this protruding part is plated with gold, and a gel-form ion permeable substance 10 is used as an intermediate layer. Thus, the pin that is merely a metal rod is used as a pseudo-reference electrode 3. In the embodiment, the pH sensor 1 uses such pseudo-reference electrode 3 having a configuration as mentioned above. According to the invention, a reference electrode includes the pseudo-reference electrode.

The abovementioned ISFET 2 is an example of an ion sensing part, and an ion selective membrane 2a that responds to pH, is provided on the upper surface part of ISFET 2. Though with this invention, the type of ion sensing part is not limited to ISFET 2, by using ISFET 2 as the ion sensor, the pH sensor can be made compact. Also, the above-described pH sensor 1 can be formed inexpensively.

Reference numeral 9 is a cover member (referred to hereinafter as "can"), which is welded to stem 4 after the insulation processing by the above-described sealing material 8 has been provided, and has an opening 9a formed near the abovementioned ion selective membrane 2a of ISFET 2. Reference numeral 10 is a gel-form ion permeating material that has been poured into can 9 from the abovementioned opening 9a.

The ion permeable substance 10 is prepared so that its pH is at predetermined value e.g. 7 and has the property of changing in pH in response to ions that enter from the exterior and exhibiting very little pH buffer action so as to permit the changing in pH. With the present specification, this property that exhibits very little buffer action, and pH is changed due to influence of ion passing the substance shall be referred to as ion permeability. A substance having ion permeability shall be referred to as an ion permeable substance. That is, it is essential for the ion permeable substance 10, sealed inside can 9, to exhibit very little buffer action to ions from the exterior so as to permit the changing in pH, and a standard solution, which is used normally for the calibration of a pH sensor, cannot be used as ion permeable substance 10, even if it is arranged in the form of a gel.

The ion permeable substance 10 that is sealed inside the abovementioned can 9 must be filled so as to cover without fail the reference electrode 3 and the ion selective membrane 2a, formed on the surface part of ISFET 2, and preferably has a viscosity such that it will not leak out from can 9 even if can 9 is set on its side or turned upside down. Furthermore, ion permeable substance 10 is filled so as to rise slightly above the abovementioned opening 9a.

Though the position at which the opening 9a is formed is preferably close to ion selective membrane 2a, it is preferable that opening 9a be located away from reference electrode 3. According to this structure, when a measurement object is pressed to the ion permeable substance 10 near the opening 9a, ion is moved at a certain part of the ion permeable substance 10 between the opening 9a and the ISFET 2, but not whole of the ion permeable substance 10. The ion is not moved to the ion permeable substance 10 around the reference electrode 3, therefore, pH is not changed there. Thus, a pseudo-reference electrode is formed. Therefore, the opening 9a may thus be formed at a position that is shifted to the left with respect to the central part of can 9 in the view from the front shown in FIG. 1. Also, in order to securely prevent pH of the ion permeable substance 10 around the reference electrode 3 from changing due to movement of ion from the opening 9a even when the measurement object is pressed to the ion permeable substance 10 near the opening 9a, a wall (barrier), which substantially obstructs and prevent the movement of ions in the parts between sealing material 8 and can 9, may be formed between reference electrode 3 and opening 9a. Thus, a moving direction of ion which tends to move toward the reference electrode 3 from the opening 9a is changed, or such ion is detoured.

Figure 2:
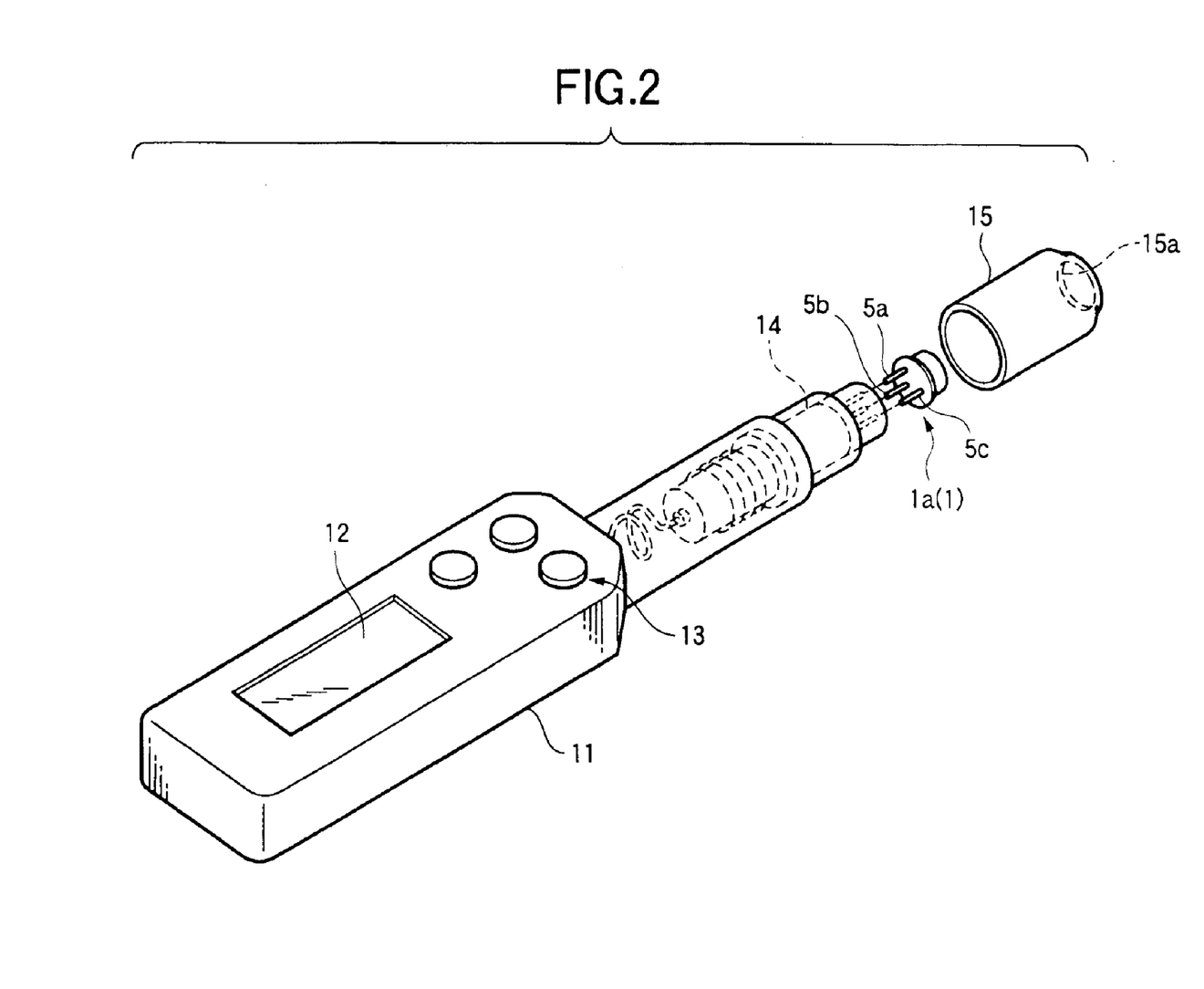
FIG. 2 is a diagram, which shows an example of a pH meter that uses the abovementioned pH sensor.

FIG. 2 is a perspective view, which schematically shows the arrangement of a pH meter 11 with which pH sensor 1 shown in FIG. 1 is arranged to be mounted in a detachable manner by means of the abovementioned pins 5a to 5c. That is, the pH sensor 1 shown in FIG. 1 is arranged as a pH sensor package 1a, which enables measurements upon the exchanging of ISFET 2, reference electrode 3, ion permeable substance 10, and can 9 according to the object to be measured.

In FIG. 2, 12 indicates a pH display part, 13 indicates operation keys of the pH meter, 14 indicates the mounting part of the pH sensor package 1a, and 15 indicates a cover, which has an opening 15a formed on the bottom part.

That is, pH sensor package 1a can be mounted to pH meter 11 by mounting cover 15 with pins 5a to 5c being inserted into the mounting part 14. Also, the pH sensor package 1a can be exchanged by removing cover 15, exchanging pH sensor package 1a with a new package, and thereafter mounting cover 15 again.

Figure 3:
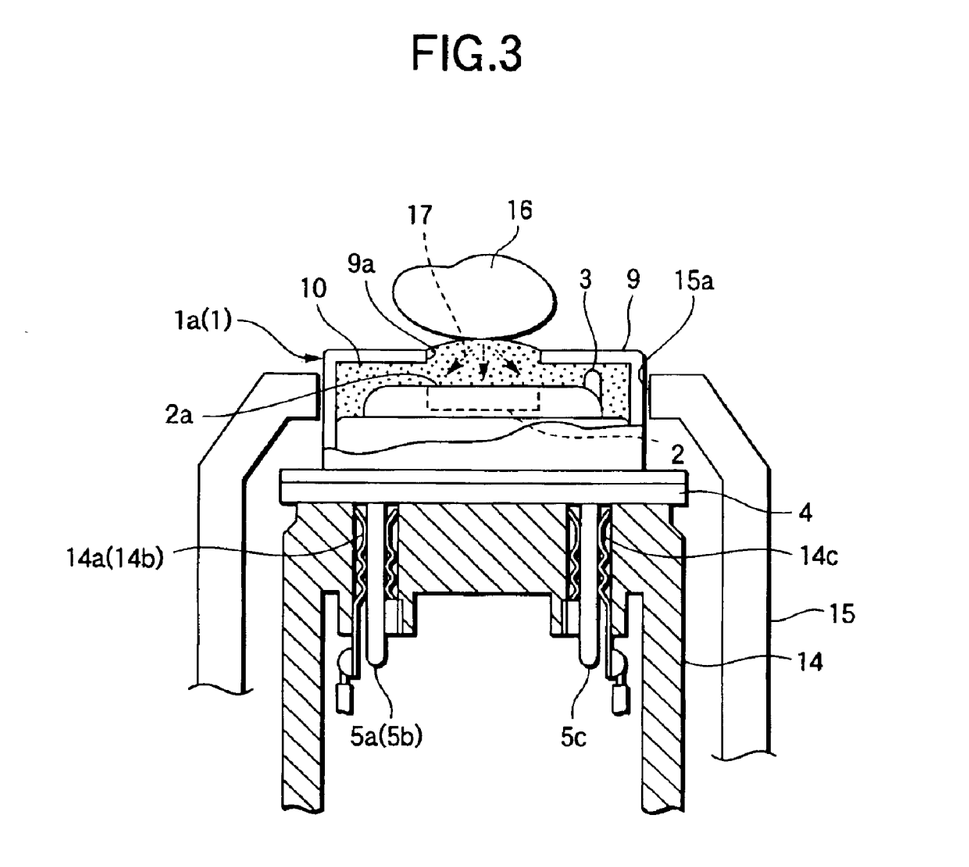
FIG. 3 is a diagram for explaining the manner in which pH is measured using the abovementioned pH sensor.

FIG. 3 is a diagram, which shows in enlarged manner the front end part of pH meter 11 in the condition where pH sensor package 1a has been set. That is, arrangements are made so that the ISFET 2 of pH sensor package 1a is connected to the circuit of pH meter 11 by inserting the pins 5a to 5cinto female connectors 14a to 14c.

When a solid substance, such as a rice grain 16, is pressed as the measured object against the opening 9, ions dissolve from the surface of rice grain 16 due to the contact of the surface of rice grain 16 with ion permeable substance 10. These ions furthermore permeate into ion permeable substance 10 as indicated by the hypothetical line arrows 17 and reach the surface part of ISFET 2 at which ion selective membrane 2a is formed.

The pH of the ion permeable substance 10 at the part at which the ion selective membrane 2a of ISFET 2 is formed thus changes from the predetermined pH value, (in this embodiment pH 7) and this change can be detected by ISFET 2.

Figure 4:
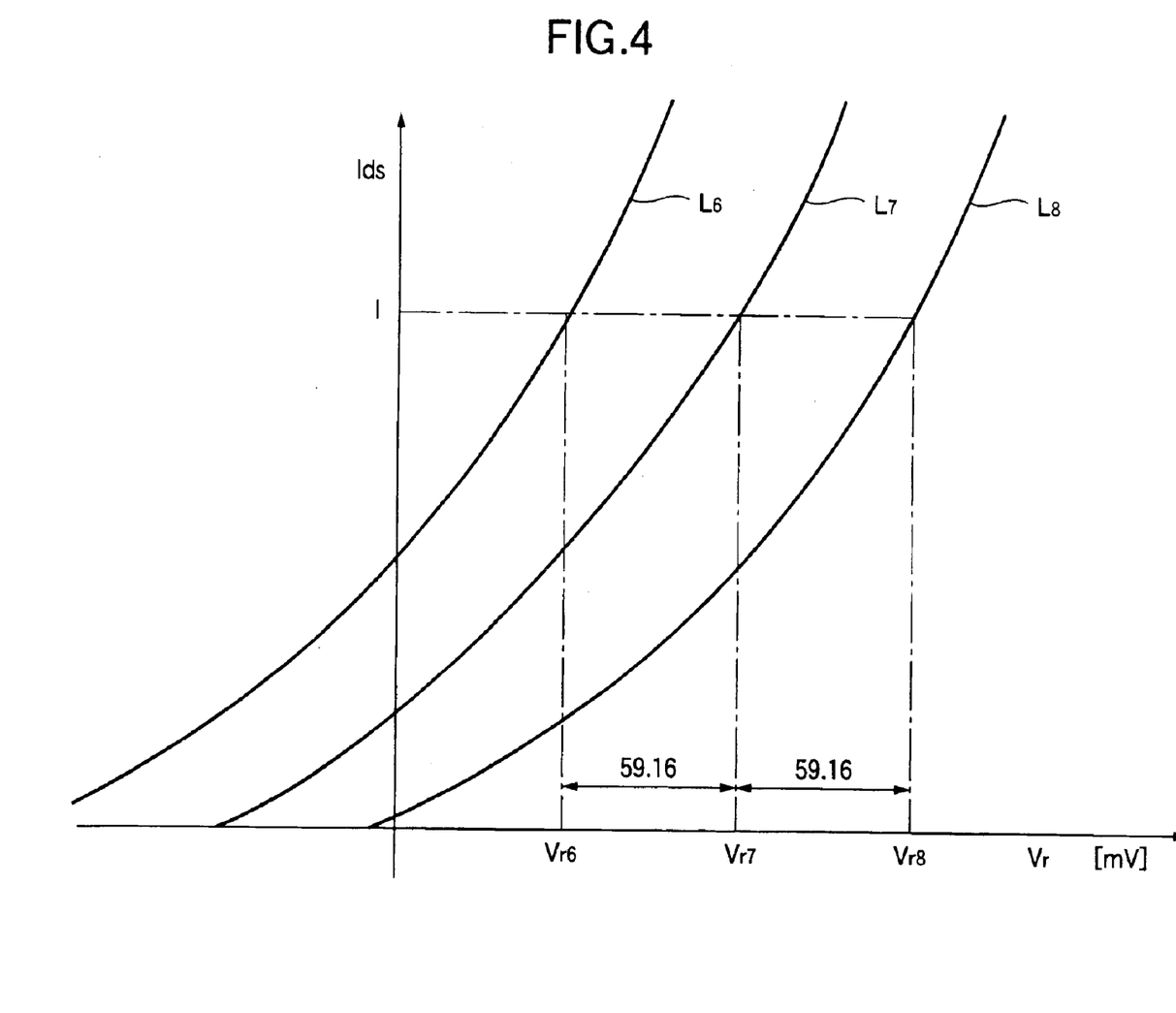
FIG. 4 is a diagram, which shows the characteristics of an ISFET.

FIG. 4 is a diagram, which shows the characteristics of ISFET 2. In FIG. 4, the abscissa indicates the voltage Vr applied to reference electrode 3 and the ordinate indicates the current Ids that flows through ISFET 2. $L_6$, $L_7$, and $L_8$ are curves that respectively indicate the Vr-Ids characteristics when the pH of the ion permeable substance 10 near the ion selective membrane 2a is 6, 7, and 8.

As shown in FIG. 4, the characteristics curves $L_6$ to $L_8$ vary so as to ideally change by 59.16 [mV] (pH sensitivity) in the abscissa direction (voltage) when the pH changes by 1. Thus with pH meter 11, by adjusting the voltage Vr applied to pin 5c so that the current Ids that flows between the two pins 5a and 5b will be of a predetermined value I, the pH of ion permeable substance 10 near ion selective membrane 2a can be determined.

In particular, since with the pH sensor 1 of this embodiment, the pH of ion permeable substance 10 is set to the predetermined value 7, the voltage applied to pin 5c prior to pressing rice grain 16 against opening 9a can be set to the voltage value $V_{r_7}$ for pH 7 so that the current Ids, which flows across the two pins 5a and 5b, will take on the predetermined value I. By then dividing the voltage change that arises by the pressing of rice grain 16 by the pH sensitivity, the magnitude of the pH shift from pH 7 can be determined.

By determining the magnitude of the pH of the ion permeable substance 10 shifted from pH 7 due to the pressing of rice grain 16, the amount of fatty acid on the surface of rice grain 16 can be determined to measure the freshness of rice. A pH meter 11 thus enables the pH of the surface of rice grain 16 to be measured accurately without performing a calibration procedure using a standard solution in particular. This measured pH value or the freshness of rice is then displayed on the display part 12 shown in FIG. 2.

In particular, since the gel-form ion permeable substance 10 is used as a mediate layer to measure the surface of a solid sample, pH measurement of a solid substance can be made extremely readily without worry of outflow of the ion permeable substance 10. The use of the gel-form ion permeable substance 10 as a mediate layer also makes possible the arrangement wherein a pin, which is merely a metal rod, is used as pseudo-reference electrode 3.

This invention however is not limited to the forming of reference electrode 3 by a metal pin 5c. That is, obviously an electrode, with which the potential is determined by ions contained in the gel-form ion permeable substance 10 (for example an Ag/AgCl electrode in the case where $Cl^-$ ions are contained in the gel), or an ordinary reference electrode may also be used as reference electrode.

Though in the description given above, a rice grain 16 was given as an example of a solid substance that is to be the measured object, and it was disclosed that by measuring the pH of the surface of this rice grain 16, the amount of fatty acid on the surface of rice grain 16 can be determined to measure the freshness of rice, this invention is obviously not limited to rice grain 16 with regard to the measured object. Also, as long as the outflow of ion permeable substance 10 does not occur with the pH sensor of the present invention, modifications for measurement of the pH value of liquids and gases which show properties thereof may be considered as well.

Furthermore, though the example of a handy-type pH meter 11 as shown in FIG. 2 was disclosed in the above description, the pH meter using the pH sensor 1 of this invention is not limited to such a handy-type pH meter.

Also, besides the ISFET, a LAPS (Light Addressable Potentiometric Sensor) type sensor, comprised of an Si substrate, may be used as the ion sensing part in the above-described arrangement of pH sensor 1.

Figure 5:
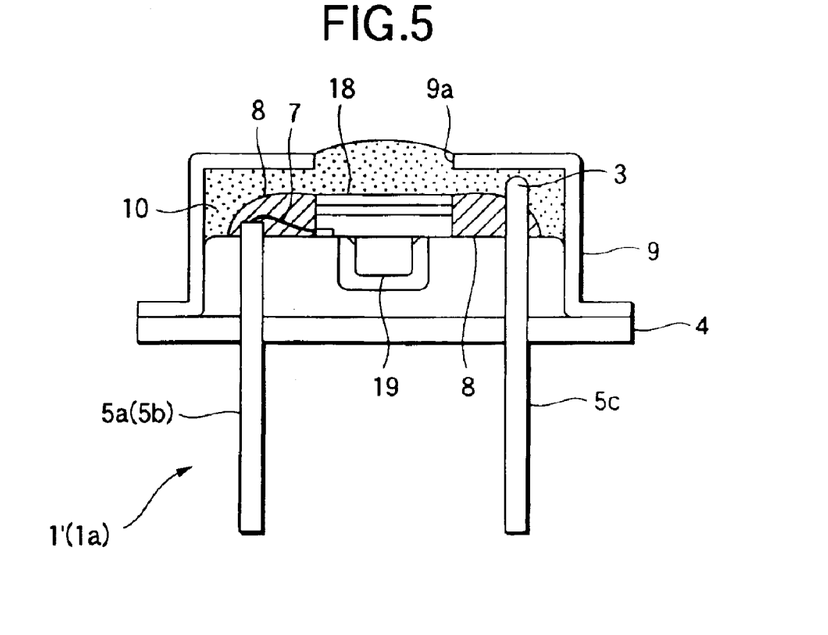
FIG. 5 is a diagram, which shows a modification of the abovementioned pH sensor.

FIG. 5 is a diagram, which shows an example of a pH sensor 1', which uses an LAPS type sensor as the ion sensing part in place of ISFET 2. Since in FIG. 5, members provided with the same symbols as those of FIG. 1 are the same as or equivalent to those shown in FIG. 1, a detailed description of these members shall be omitted.

In FIG. 5, 18 is a LAPS type semiconductor pH sensor and 19 is a light emitting diode, which supplies excitation light to this pH sensor. That is, with the pH sensor 1' of this example, the pH value can be measured by measuring the photo-current that flows through the LAPS type semiconductor pH sensor 18 in the condition where light emitting diode 19 is intermittently emitted.

Figure 6:
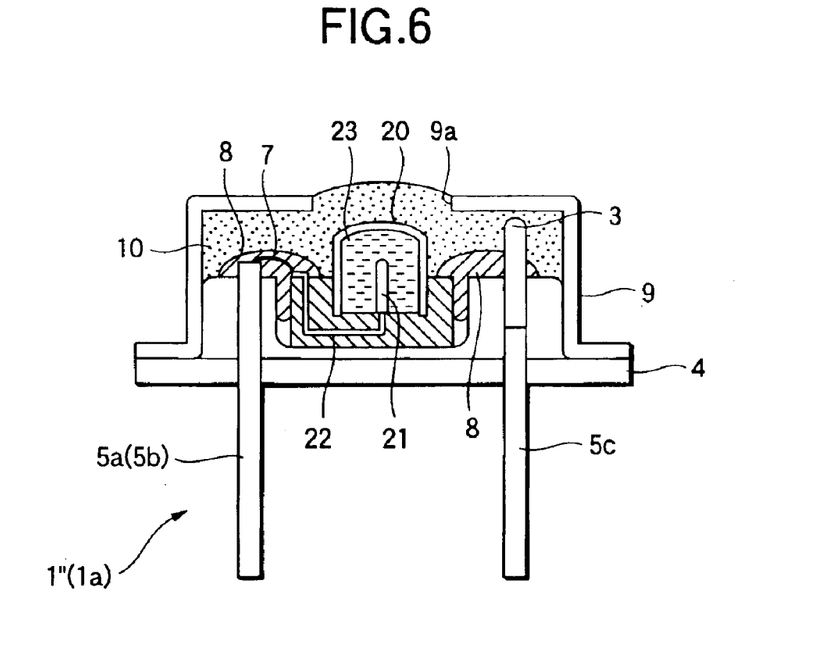
FIG. 6 is a diagram, which shows another modification of the abovementioned pH sensor.

FIG. 6 is a diagram, which shows an example of a pH sensor 1", which uses pH glass electrode as the ion sensing part. Since in FIG. 6, members provided with the same symbols as those of FIG. 1 are the same as or equivalent to those shown in FIG. 1, a detailed description of these members shall be omitted.

In FIG. 6, 20 is a glass membrane, which is an example of an ion sensing part, 21 is an inner electrode, which is sealed in the interior of glass membrane 20, 22 is a lead wire for connection of inner electrode 21 to leader line 7, and 23 is an internal solution, which is sealed inside the glass membrane.

Though with all of the examples described above, a pH sensor package 1a is formed from pH sensor 1, 1', or 1" and this pH sensor package 1a is arranged to be detachable with respect to pH meter 11, this invention is not limited to this arrangement.

As has been described above, by using a pH sensor by this invention and pressing an object to be measured against the opening formed on the cover member, the pH value of the ion permeable substance changes due to being affected by properties of the surface of the measured object, and this change of pH value can then be measured by the ion sensing part. Also, since the pH value of the ion permeable substance prior to making the measurement is known, this can be used as the reference pH value, thus doing away with the calibration of the pH sensor using standard solution. Further, the ion permeable substance is in a form of a gel, the surface of a solid substance can be measured simply and yet at high sensitivity with use of the ion permeable substance as a mediate layer.

What is claimed is:

1. A pH sensor comprising:
   an ion sensing part of an ion sensor, which responds to pH;
   a reference electrode;
   a gel-form ion permeable substance, which has a predetermined pH value and covers the ion sensing part and the reference electrode; and
   a cover member which houses the ion permeable substance and has an opening formed at a position close to said ion sensing part;
   wherein said opening allows a measurement object to be pressed against said gel-form ion permeable substance at said opening.

2. A pH sensor as claimed in claim 1, wherein said gel-form ion permeable substance has a property of changing in pH in response to ions that enter from an exterior and exhibiting very little pH buffer action so as to permit the changing in pH.

3. A pH sensor as claimed in claim 2, wherein said gel-form ion permeable substance is prepared to be pH 7.

4. The pH sensor as claimed in claim 1, wherein said gel-form ion permeable substance is filled so as to rise slightly above said opening.

5. The pH sensor as claimed in claim 1, wherein said opening is located away from said reference electrode.

6. The pH sensor as claimed in claim 1, wherein said measurement object is solid matter.

7. A combination, comprising:
   a measurement object; and the pH sensor as claimed in claim 1,
wherein the measurement object is pressed against said gel-form ion permeable substance at said opening.

8. The combination as claimed in claim 7, wherein the measurement object is a solid matter.

9. A pH sensor comprising:
an ion sensitive field effect transistor, arranged by the provision of an ion selective membrane, which responds to pH, on the gate of a field effect transistor;
a reference electrode;
a gel-form ion permeable substance, which has a predetermined pH value and covers at least said ion selective membrane and the reference electrode; and
a cover member which houses the ion permeable substance and has an opening formed at a position close to said ion selective membrane;
wherein said opening allows a measurement object to be pressed against said gel-form ion permeable substance at said opening.

10. A pH sensor as claimed in claim 9, wherein said gel-form ion permeable substance has a property of changing in pH in response to ions that enter from an exterior and exhibiting very little pH buffer action so as to permit the changing in pH.

11. A pH sensor as claimed in claim 10, wherein said gel-form ion permeable substance is prepared to be pH 7.

12. The pH sensor as claimed in claim 9, wherein said gel-form ion permeable substance outwardly protrudes from the opening.

13. The pH sensor as claimed in claim 9, wherein said opening is located away from said reference electrode.

14. The pH sensor as claimed in claim 9, wherein said measurement object is solid matter.

15. A pH meter device comprising:
a pH sensor including an ion sensing part of an ion sensor which responds to pH, a reference electrode, a gel-form ion permeable substance, which has a predetermined pH value and covers the ion sensing part and the reference electrode, and a cover member which houses the ion permeable substance and has an opening formed at a position close to said ion sensing part; and
a device body including a pH display part, operation keys, and mounting part to which said pH sensor is detachably mounted;
wherein said opening allows a measurement object to be pressed against said gel-form ion permeable substance at said opening.

16. The pH sensor as claimed in claim 15, wherein said gel-form ion permeable substance outwardly protrudes from the opening.

17. The pH sensor as claimed in claim 15, wherein said opening is located away from said reference electrode.

18. The pH sensor as claimed in claim 15, wherein said measurement object is solid matter.

19. A pH meter device comprising:
a pH sensor comprising an ion sensitive field effect transistor, arranged by the provision of an ion selective membrane, which responds to pH, on the gate of a field effect transistor, a reference electrode, a gel-form ion permeable substance, which has a predetermined pH value and covers at least said ion selective membrane and the reference electrode, and a cover member which houses the ion permeable substance and has an opening formed at a position close to said ion selective membrane; and
a device body including a pH display part, operation keys, and mounting part to which said pH sensor is detachably mounted wherein said opening allows a measurement object to be pressed against said gel-form ion permeable substance at said opening.

20. The pH sensor as claimed in claim 19, wherein said gel-form ion permeable substance outwardly protrudes from the opening.

21. The pH sensor as claimed in claim 19, wherein said opening is located away from said reference electrode.

22. The pH sensor as claimed in claim 19, wherein said measurement object is a solid matter.

* * * * *